US007714127B2

United States Patent
Li et al.

(10) Patent No.: US 7,714,127 B2
(45) Date of Patent: May 11, 2010

(54) PROCESS FOR MAKING HETEROARYL AMINE INTERMEDIATE COMPOUNDS

(75) Inventors: Guisheng Li, Glen Allen, VA (US); Jianxiu Liu, Richmond, VA (US); Zhi-Hui (Bruce) Lu, Glen Allen, VA (US); Ming Shen, Waltham, MA (US); Sonia Rodriguez, New Milford, CT (US); Vittorio Farina, Ridgefield, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 789 days.

(21) Appl. No.: 11/538,465

(22) Filed: Oct. 4, 2006

(65) Prior Publication Data

US 2007/0105857 A1 May 10, 2007

Related U.S. Application Data

(60) Provisional application No. 60/724,263, filed on Oct. 6, 2005.

(51) Int. Cl.
*C07D 413/06* (2006.01)
(52) U.S. Cl. ..................................... 544/124
(58) Field of Classification Search ................. 544/124
See application file for complete search history.

(56) References Cited

U.S. PATENT DOCUMENTS

| 6,080,763 | A | 6/2000 | Regan |
| 6,319,921 | B1 | 11/2001 | Cirillo |
| 6,358,945 | B1 * | 3/2002 | Breitfelder et al. ....... 514/227.8 |
| 6,608,052 | B2 | 8/2003 | Breitfelder et al. |
| 6,635,767 | B2 | 10/2003 | Song |
| 7,022,883 | B2 * | 4/2006 | Song et al. .................. 564/387 |
| 7,196,219 | B2 * | 3/2007 | Scherer et al. ................. 564/8 |

FOREIGN PATENT DOCUMENTS

| WO | WO 00/55139 | | 9/2000 |
| WO | WO 01/32627 | A1 | 5/2001 |
| WO | WO 02/083642 | A1 | 10/2002 |

OTHER PUBLICATIONS

Kitigawa et al. Angew. Chem. Int. Ed. 2000, 39, 2481-2483.*
Miyaura, N.; Palladium-Catalyzed Cross-Couplilng Reactions of Organoboron Compounds with Organic Halides; Chem. Rev., 1995, 95, 2547-2483.
Diederich, F.; Metal-catalyzed cross-coupling reactions; Eds. Wiley-VCH: Weinheim, Germany, 1998, Chapter 2, 49-97.

* cited by examiner

*Primary Examiner*—Rebecca L Anderson
*Assistant Examiner*—Matthew P Coughlin
(74) *Attorney, Agent, or Firm*—Michael P. Morris; Anthony P. Bottino; Edward S. Lazer

(57) ABSTRACT

Disclosed are processes to produce a compound of the formula (I):

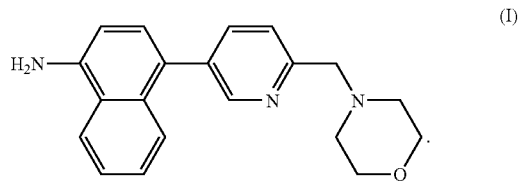

(I)

8 Claims, No Drawings

PROCESS FOR MAKING HETEROARYL AMINE INTERMEDIATE COMPOUNDS

APPLICATION DATA

This application claims benefit to U.S. provisional application Ser. No. 60/724,263, filed Oct. 6, 2005.

BACKGROUND OF THE INVENTION

1. Technical Field

This invention relates to a process of making heteroaryl amine intermediates.

2. Background Information

Aryl- and heteroaryl-substituted ureas have been described as inhibitors of cytokine production and effective therapeutics in cytokine-mediated diseases including inflammatory and autoimmune diseases. Examples of such compounds are reported in U.S. Pat. Nos. 6,080,763 and 6,319,921, and WO 00/55139 including aryl- or heteroaryl-substituted ureas.

In U.S. Pat. No. 6,358,945 the synthesis of II, a preferred intermediate, was described as illustrated in Scheme 1.

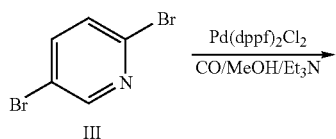

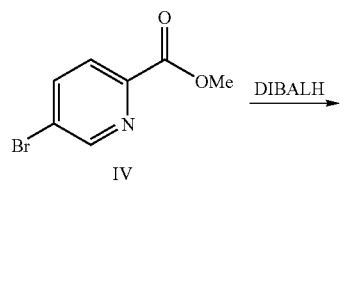

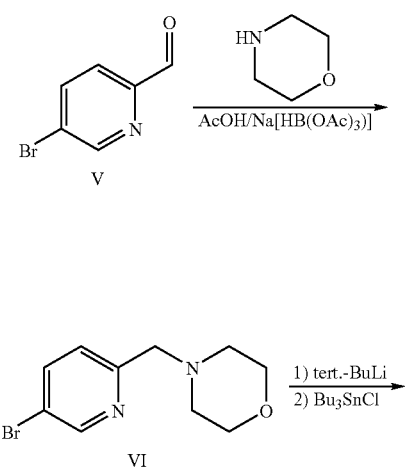

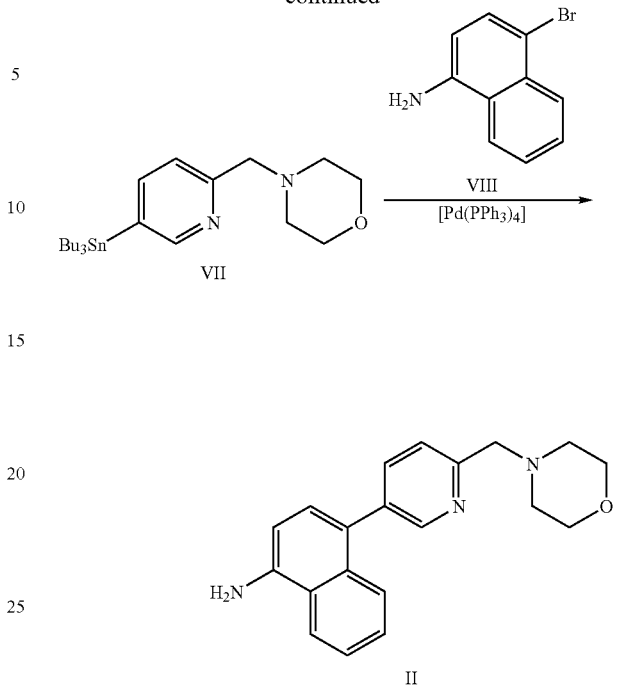

The synthesis begins with a palladium catalyzed carbonylation of 2,5-dibromopyridine (III) to provide ester IV in 55% yield. The reaction is run under pressure (80 psi CO) and must be monitored to minimize formation of the diester, an unwanted by-product. Reduction of IV with diisobutylaluminum hydride at −78° C. provides aldehyde V. This is followed by reductive amination to give VI.

Intermediate VI is then converted to II by reaction with t-BuLi at −78° C. followed by tributyltin chloride to give tributylstannane VII, followed by palladium catalyzed Stille coupling with intermediate VIII to give II. Conversion of VI and analogous intermediates to other intermediates of formula II via Suzuki coupling is also described in U.S. Pat. No. 6,358,945 (Scheme 2). According to this method, intermediate IX is treated with n-BuLi followed by trimethylborate to give arylboronic acid X. Palladium catalyzed Suzuki coupling with VI provides XI, which is deprotected by treatment with acid to give II.

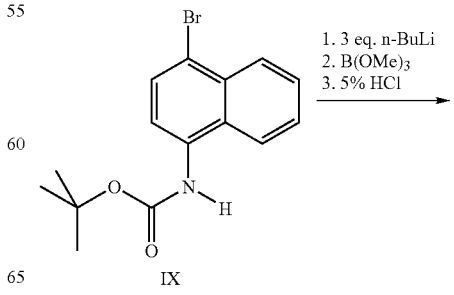

-continued

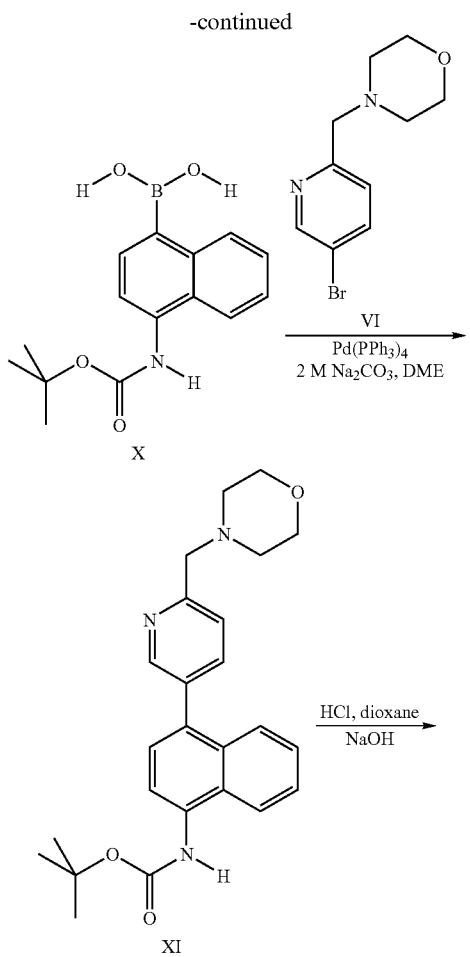

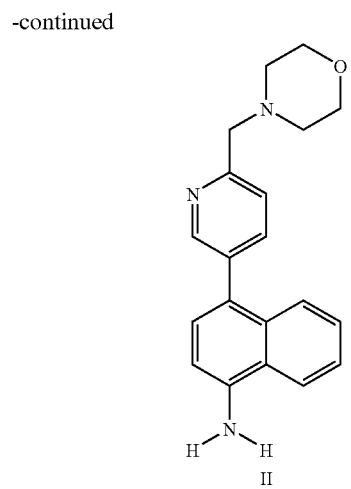

This process is not well-suited for large-scale and commercial use for several reasons. One reaction (Scheme 1) is run under high pressure (80 psi) and another at extreme temperature (−78° C.). The yield of IV is only moderate and by-product formation requires a purification step. These factors, plus the cost of starting materials and reagents make this process too costly for commercial scale.

U.S. Pat. No. 6,635,767 discloses a process of making compound II above involving reacting 2-(5-halopyridyl) magnesium halides 3, with an in situ generated immonium salt electrophile 6 as shown below in Scheme 3, or alternatively by reacting with a formyl bearing group e.g. 7.

Scheme 3

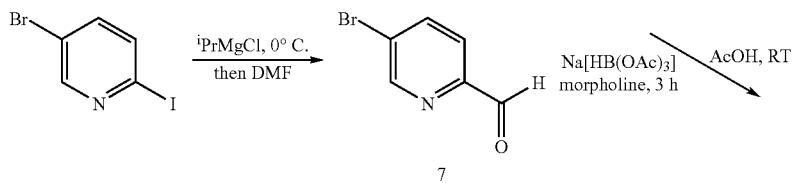

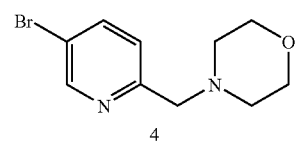

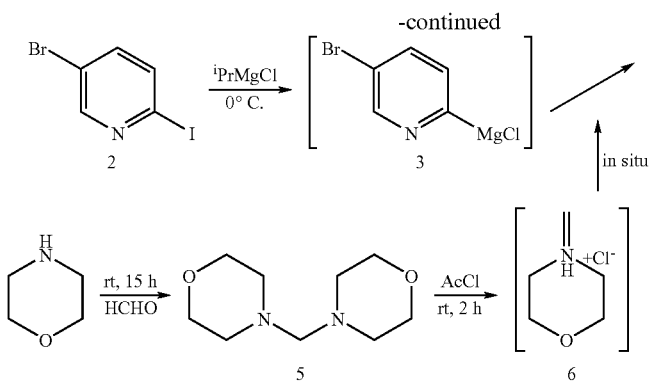

Reaction intermediate 4 is then reacted with 9 as can be seen in Scheme 4 which also shows the conversion of 7 to 9.

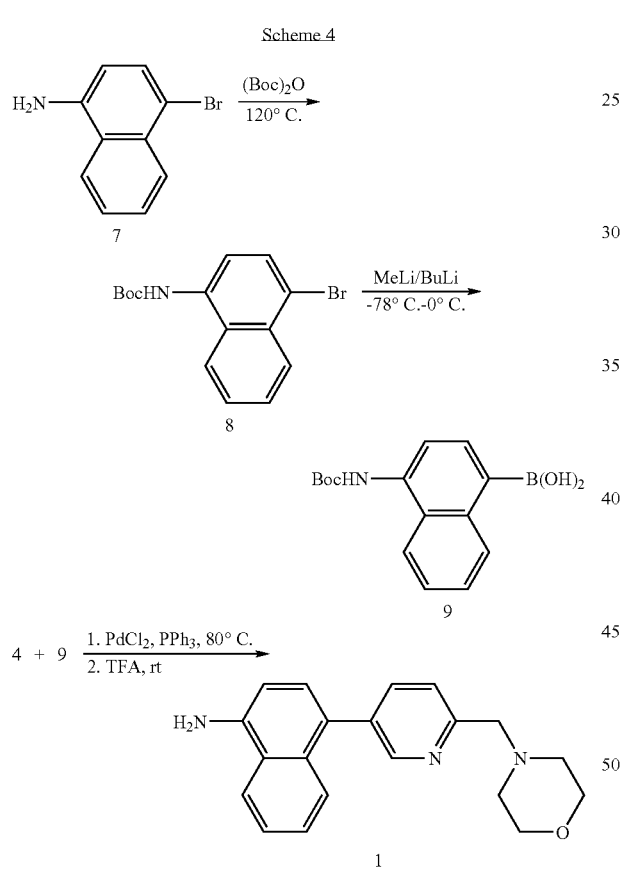

Other related reactions can be found in WO 01/32627, WO 02/083642, Miyaura, N.; Suzuki, A. Chem Rev. 1995, 95, 2457-83; Suzuki, A. in Metal-catalyzed Cross-coupling Reactions; Diederich, F,; Stang, P. J. Eds. Wiley-VCH: Weinheim, Germany, 1998, chapter 2, 49-97.

BRIEF SUMMARY OF THE INVENTION

It is therefore an object of the invention to provide an improved process to produce a compound of the formula (I), the isomers and analogs thereof:

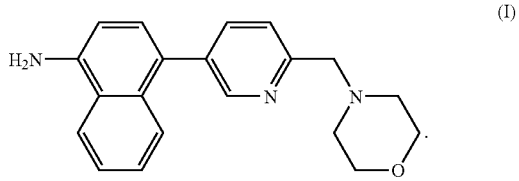

DETAILED DESCRIPTION OF THE INVENTION

Four practical processes have been developed for preparation of compounds of the formula (I).(Scheme 5-8)

a) The first process involves the in-situ protection of 1-amino-4-bromonaphthalene as the bis-TMS analog followed by the sequence of metallation/borylation/Suzuki coupling to give 90% isolated yield of the desired compound I (Scheme 5). The identification of optimal conditions to conduct the sequence in one-pot is not trivial. Specifically, (1) it is novel to form 4-bromo-N,N-bis(trimethylsilyl)aminonaphthalene under non-cryogenic condition (0-5° C.) using n-HexLi/TMSCl in MTBE to avoid Br—Li exchange at this step. The proper choice of solvent is crucial to avoid side reactions; (2) it is novel to identify the proper magnesiate reagent (i-PrR$_2$MgLi, R=C$_1$-C$_{12}$ branched or unbranched alkyl) for successful preparation of the N,N-bis(trimethylsilyl)aminonaphthyl anion via the bromo-magnesium exchange; (3) it is novel to demonstrate that the Suzuki coupling process could proceed successfully using the mixture of the boronic acid and borinic acid generated in-situ. This practical process obviated the traditional tedious procedure to purify the boronic acid before proceeding to the Suzuki coupling reaction.

b) The second process involves the metallation of the tert-butyl N-(4-bromonaphthyl)-carbamate by using sequentially n-BuLi as base for deprotonation and magnesiate reagent (i-PrR$_2$MgLi, R=C$_1$-C$_{12}$ branched or unbranched alkyl) for preparation of the corresponding anion via the bromo-magnesium exchange; Trapping of the anion with a borate to form the mixture of boronic and borinic acid, followed by Suzuki coupling reaction produced the N—tert-butyl carbamate analog of the desired product in 80-88% yield. Conversion of the carbamate to the target compound (I) is readily achieved by the classical method of using hydrogen chloride to cleave the protecting group (Scheme 6).

c) A preferred route is the third process (Scheme 7). This novel one-pot process involves the following sequence of metallation/borylation/Suzuki coupling. Specifically, reaction of 4-[2-(5-bromo-pyridinylmethyl)]morpholine with i-Pr(Bu)$_2$MgLi at approximately −20° C. gives a tripyridine magnesiate intermediate, which reacts with trimethylborate at approximately −18° C. to afford the corresponding boronate. Without isolation of aqueous soluble boronic acid, the mixture is charged with 1-amino-4-bromonaphthalene, palladium acetate, triphenylphosphine, an aqueous solution of potassium phosphate, and 2-propanol (IPA). The contents are heated to 80° C. until consumption of the boronic acid is complete. The product is isolated as the corresponding HCl salt in 84-88% overall yield. The process highlights the following novel feature: the successful generation of the 2-[(4'-morpholine)methyl]-5-pyridyl anion via direct magnesium-bromide exchange, using the magnesiate reagent (i-PrR$_2$MgLi, R=C$_1$-C$_{12}$ branched or unbranched alkyl). 4-[2-(5-bromo-pyridinylmethyl)]morpholine contains two acidic methylene protons which are prone to deprotonation by strong bases such as Grignard reagent, therefore preventing the bromo-magnesium exchange. It is crucial to use the more reactive magnesiate reagent to achieve the Mg—Br exchange.

The fourth approach involves a 7-step process to prepare the target compound I without the use of palladium catalysis or organometallic reagents. The key step is the reaction of a vinamidinium salt with acetone to form the pyridine ring (Scheme 8).

The terms below shall be defined as follows:
n-HexLi: n-hexyl lithium
TMSCI: trimethylsily chloride
MTBE: methyl tert-butyl ether
i-Pr: isopropyl;
Bu: n-butyl;
Et: ethyl;
THF: tetrahydrofuran
TMS: trimethylsily
Hex: n-hexyl
OMe: methoxy;
MeOH: methanol;
Ar: aryl;
OAc: acetate;
PPh$_3$: triphenylphosphine;
IPA: isopropanol;
IPAc: isopropyl acetate;
Boc: tert-butoxycarbonyl;
DME: 1,2-dimethoxyethane;
r.t.: room temperature;
LiHMDS: lithium bis(trimethylsilyl)amide;
TCC: trichloroisocyanuric acid.

The compound of formula (I) can exist in more than one tautomeric form. The invention includes methods producing all such tautomers.

The processes of the invention also include making isotopically-labelled forms of the formula (I). An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. A pharmaceutically acceptable salt of either which contains none, or one or more of the above-mentioned isotopes and/or other isotopes of other atoms is contemplated to be within the scope of the present invention.

In one generic aspect, there is provided a first process of making a compound of the formula (I), the tautomers, isomers and analogs thereof:

said process comprising:

in step 1, providing a naphthylamine compound (a) in n-HexLi plus TMSCI under suitable conditions and solvent, preferably MTBE at 0 to 20° C. to provide compound (b);

in step 2, adding i-Pr(n-Hex)$_2$MgLi to (b) to produce compound (c);

in step 3, adding B(OMe)$_3$ to (c) to produce compound (d);

in step 4 adding compound (e) to (d) under suitable conditions, preferably Pd(OAc)$_2$, PPh$_3$, K$_2$CO$_3$, IPA, and subsequently isolating product compound (I) as its acid salt by adding acid, preferably HCl in a suitable solvent, preferably IPAc (f), product compound (I) can be converted to the free base by treatment with a base, such as sodium hydroxide.

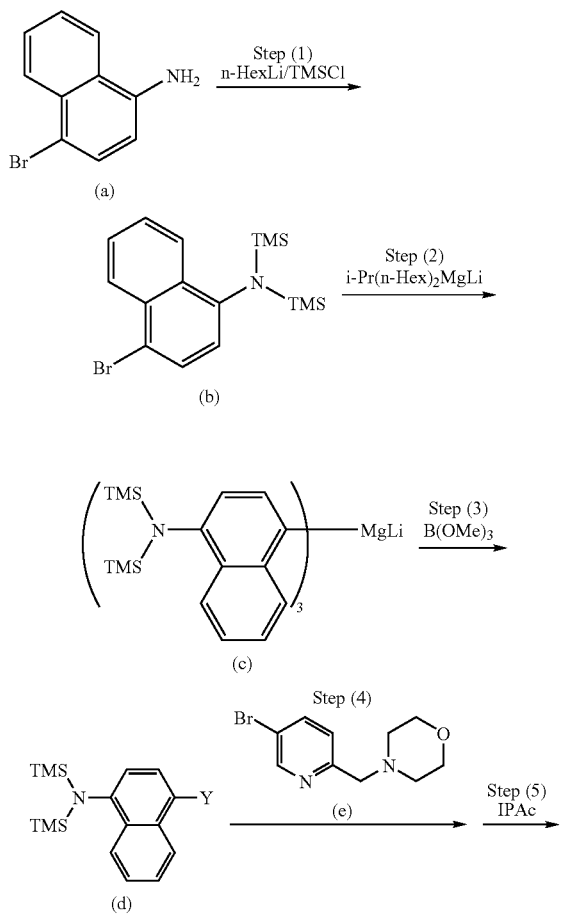

Scheme 5

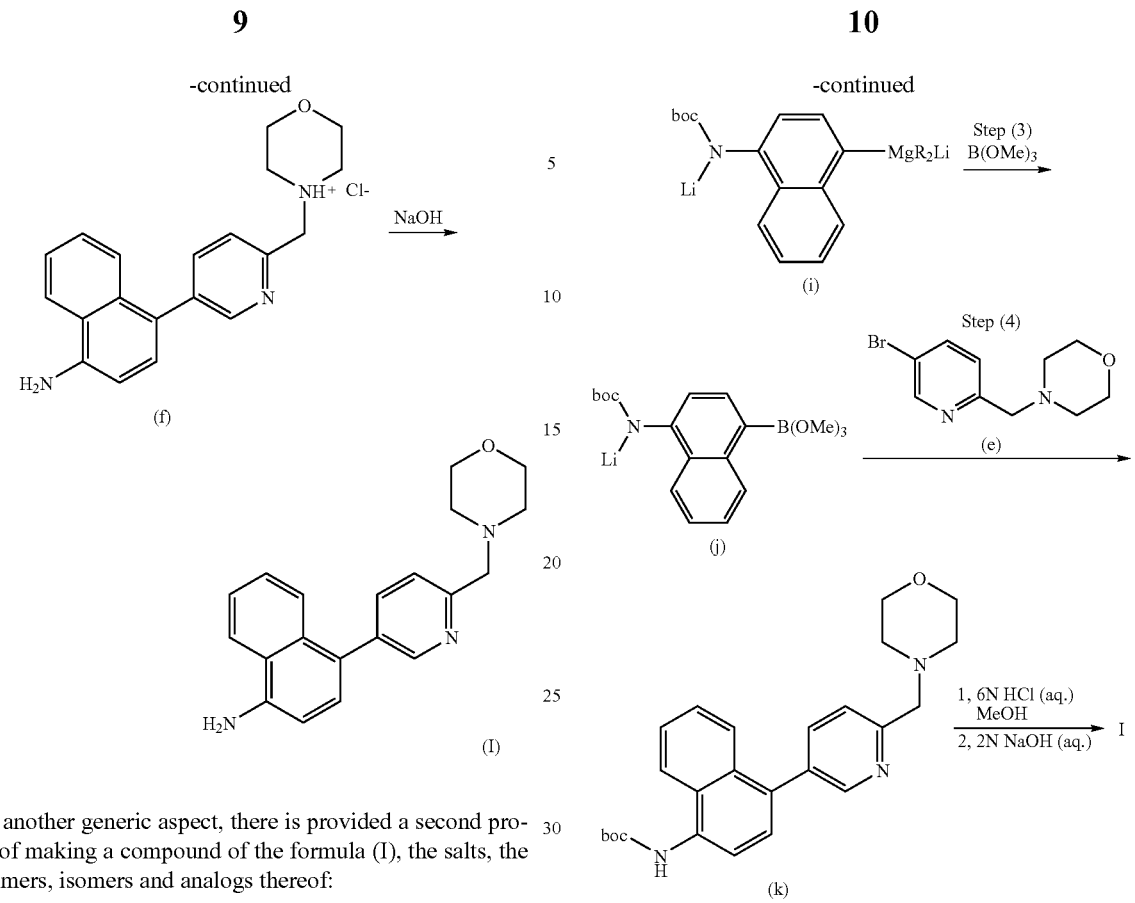

In another generic aspect, there is provided a second process of making a compound of the formula (I), the salts, the tautomers, isomers and analogs thereof:

said process comprising:

in step 1, providing a N-Boc protected naphthylamine compound (g) in n-BuLi under suitable conditions and solvent, preferably MTBE, at approximately 0-5° C. to provide compound (h);

in step 2, adding i-Pr(n-Bu)$_2$MgLi in a suitable solvent, preferably THF to (h) to produce compound (i);

in step 3, adding B(OMe)$_3$ to (i) to produce compound (j);

in step 4 adding compound (e) to (j) under suitable conditions, preferably Pd(OAc)$_2$, PPh$_3$, Na$_2$CO$_3$, DME, to produce (k), and subsequently deprotecting (k) by treatment with HCl aqueous solution in methanol and isolating product compound (I) after basifying with NaOH.

In another generic aspect, there is provided a third process of making a compound of the formula (I), the tautomers, isomers and analogs thereof:

said process comprising:

in one pot providing a 5-bromo-2-[(4-morpholino)methyl] pyridine compound (e) in i-Pr(n-Bu)$_2$MgLi under suitable conditions (<−20° C.) and solvent, preferably THF, subsequently adding B(OMe)$_3$, then adding Pd(OAc)$_2$, PPh$_3$, K$_3$PO$_4$, IPA, and 1-amino-4-bromonaphthalene (a) and subsequently HCl, IPAc and MeOH at ambient temperature to provide compound (l) as the HCl salt which can converted to the free base by treatment with a base such as NaOH.

Scheme 6

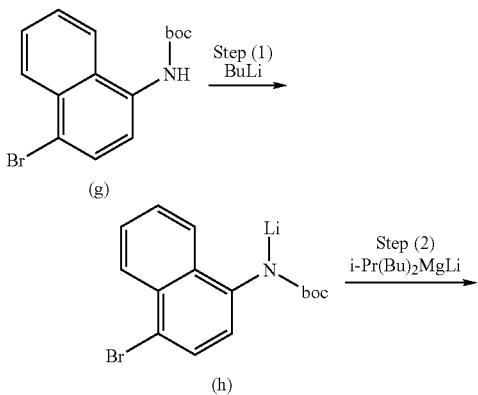

Scheme 7

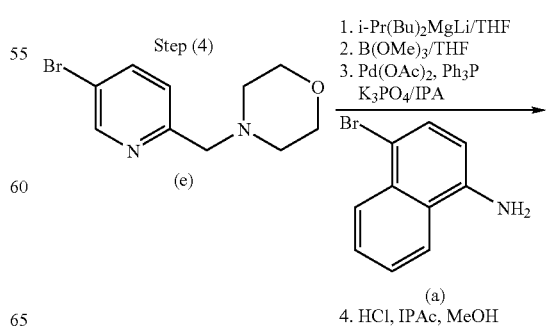

-continued (I)

In another generic aspect, there is provided a fourth process of making a compound of the formula (I), the tautomers, isomers and analogs thereof:

said process comprising:

reacting a carboxylic acid compound (m) with $POCl_3$ in a suitable solvent, such as DMF at about 70° C;

and subsequently adding aqueous $HPF_6$ and a base, preferably NaOH, at low temperature, preferably about <10° C.;

and recrystallizing the compound (n) under suitable conditions, such as $EtOH/H_2O$;

in step 2 adding acetone with LiHMDS in a suitable solvent such as THF at about 0-25° C. to produce intermediate (o);

in step 3 adding ammonium acetate to (o) to produce compound (p), subsequently in step 4 chlorinating (p) with a suitable agent such as TCC under suitable conditions, preferably at about 70° C., to produce compound (q);

adding the morpholino heterocycle in step 5 under suitable conditions, preferably about 70° C., to produce nitro compound (r) and subsequently reducing (r) in step 6 under reducing conditions, preferably $H_2$ (1 atm) and a catalyst, preferably Pd on carbon to produce (I);

Scheme 8

-continued (o)

(p)

(q)

(r)

In order that this invention be more fully understood, the following examples are set forth. These examples are for the purpose of illustrating preferred embodiments of this invention, and are not to be construed as limiting the scope of the invention in any way.

SYNTHETIC EXAMPLES

Example 1

Synthesis of N-boc-4-(6-morpholin-4-ylmethyl-pyridin-3-yl)-naphthalen-1-ylamine. One-pot borylation/Suzuki Coupling Approach via N-boc-4-bromonaphthyl-1-amine 1) n-BuLi (1 eq), MTBE, -15° C.
2) i-Pr(nBu)$_2$MgLi (0.4 eq), -15° C.
3) B(OMe)$_3$ (3.5 eq), -15° C. to rt
4) Br— (0.9 eq)

Pd(OAc)$_2$ (0.2%), PPh$_3$ (0.8%)
Na$_2$CO$_3$ (5 eq)
H$_2$O, DME, 80° C., 2 h

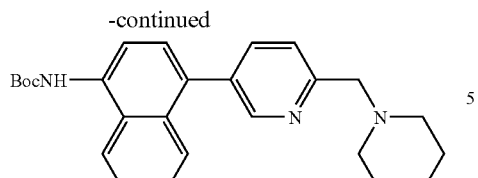

To a solution of N-Boc-4-bromonaphthyl-1-amine (10.0 g, 31.2 mmol, 1.0 eq) in anhydrous t-butyl methyl ether (MTBE) (80 mL) at −15° C. was added 2.5 M n-BuLi in hexanes (12.5 mL, 31.3 mmol, 1.0 eq) over 1 h at −15±2° C. The green solution was stirred at −15±2° C. for 30 min before adding a 0.4 M solution of i-Pr(Bu)$_2$MgLi in THF (31 mL, 12.4 mmol, 0.4 eq) dropwise keeping the temperature at −15±2° C. The reaction mixture was further stirred at −15±2° C. for 30 min. B(OMe)$_3$ (12 mL, 107.6 mmol, 3.5 eq) was added dropwise at −12±2° C. After stirring at −12±3° C. for 1 h, the reaction mixture was allowed to warm to room temperature. Dimethoxyethane (70 mL) was added followed by 2 M aqueous Na$_2$CO$_3$ (70 mL, 140 mmol, 4.5 eq), and a mixture of 4-(5-bromo-pyridin-2-ylmethyl)-morpholine (7.21 g, 28.0 mmol, 0.9 eq), Pd(OAc)$_2$ (16 mg, 0.007 mmol, 0.002 eq), and PPh$_3$ (74 mg, 0.28 mmol, 0.009 eq). The mixture was heated to 80±5° C. while distilling the lower boiling point solvents. After 3 h, the reaction mixture was allowed to cool to 30±2° C. before adding EtOAc (40 mL). After filtration of the solids, heptane (50 mL) was added to the filtrate. After stirring at room temperature for a couple of hours, the precipitated product was collected by filtration, and rinsed with heptane. After drying under vacuum, the title compound was obtained as a white solid (9.5 g, 81% yield, 94 A % purity).

Example 2

Synthesis of 4-(6-morpholin-4-ylmethyl-pyridin-3-yl)-naphthalen-1-ylamine hydrochloride via Bis(TMS)-Protection

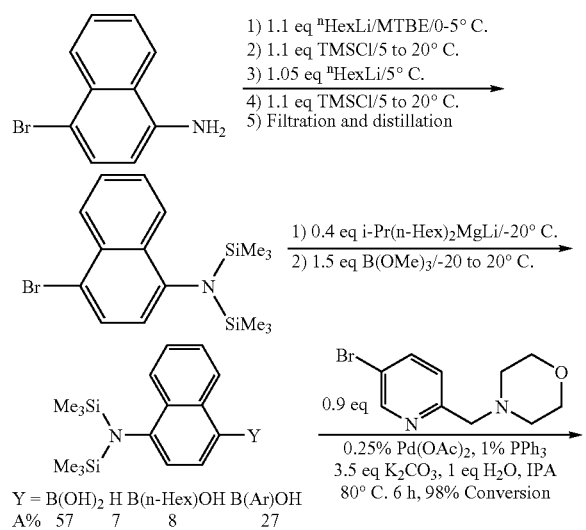

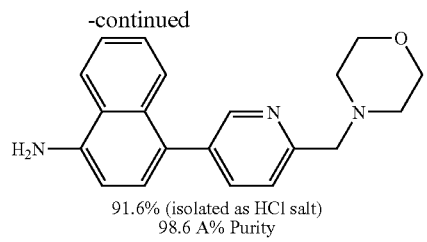

91.6% (isolated as HCl salt)
98.6 A% Purity

A suspension of 1-amino-4-bromonaphthalene (22.21 g, 100 mmol) in MTBE (133 mL) was cooled to 0° C. A solution of n-hexyllithium in hexane (2.3 M, 47.83 mL, 110 mmol) was added below 5° C. The brown-red solution was stirred at 5° C. for 15 min. Chlorotrimethylsilane (13.91 mL, 110 mmol) was slowly added while maintaining the temperature at 5° C. The grey suspension was stirred at 5° C. for 10 min and then warmed to 20° C. over 30 min. The mixture was cooled back to 0° C. and n-hexyllithium in hexane (2.3 M, 45.65 mL, 105 mmol) was added at 0 to 5° C. The yellowish suspension was stirred for 30 min before chlorotrimethylsilane (13.91 mL, 110 mmol) was slowly added at 5-10° C. The suspension was warmed up to 20° C. over 30 min. Solvents were distilled until the internal temperature reached 70° C. The white solid was filtered and rinsed with dry heptane (100 mL). The solvent was removed from the combined filtrates by distilling until 125° C. to leave a dark-brown solution. The resulting crude 1-N,N-bis(trimethylsilyl)-amino-4-bromonaphthalene was used in the next step without further purification.

To a solution of i-PrMgCl (2 M in THF, 20 mL, 40 mmol) in anhydrous THF (40 mL) at 0° C. was slowly added n-hexyllithium (2.3 M in hexane, 34.78 mL, 80 mmol) while maintaining the temperature below 5° C. The resulting solution was stirred at 0° C. for 10 min. The solution was cooled to −20° C. and the crude 1-N,N-bis(trimethylsilyl)-amino-4-bromonaphthalene in THF (10 mL) was placed in a dropping funnel and added dropwise while maintaining the reaction temperature below −15° C. After the addition, the original flask and the dropping funnel were rinsed with THF (10 mL) and the THF rinses were added to the reaction. After the addition, the brown-red solution was stirred at −20° C. until the exchange was complete as monitored by HPLC (usually it take about 20 min). Trimethylborate (17.00 mL, 150 mmol) was slowly added at a rate to maintain the inside temperature below −15° C. The dark-brown solution was stirred at −20° C. for 1 h before it was warmed up to 20° C. in 1-3 h to obtain a brown suspension.

Under nitrogen, 4-(5-bromo-pyridin-2-ylmethyl)-morpholine (23.14 g, 90 mmol), palladium acetate (56 mg, 0.25 mmol), triphenylphosphine (262 mg, 1 mmol) and potassium carbonate (48.37 g, 350 mmol) were added. Isopropanol (176 mL) and water (1.80 mL, 1 mmol) were added. The mixture was flushed with nitrogen for 5 min and heated to distill some solvents to reach 80° C. in about 1 h. The coupling was complete after 6 h. Water (100 mL) was added and the distillation was continued until the internal temperature reached 95° C. The mixture was cooled to 30° C. and isopropyl acetate (100 mL) was added followed by 11 g of diatomaceous earth. The mixture was stirred for 15 min and filtered. The solid was rinsed with isopropyl acetate (80 mL) and the organic phase was washed with water (2×100 mL). To the organic phase, MeOH (28 mL) was added, followed by 37% HCl (9.47 g, 95.4 mmol). The mixture was stirred at room temperature for 12 h and the solid was collected and washed with isopropyl acetate (112 mL). The pale yellow solid was dried in a vacuum oven (40° C./10 in Hg) to constant weight (29.39 g, 91.7% with 98.6 A % purity). $^1$H NMR (400 mHz, DMSO-$d_6$): δ 8.69 (d, J=4.0 Hz, 1H), 8.22-8.15 (m, 1H), 7.98 (dd, J=2.0 and 8.0 Hz, 1H), 7.75-7.65 (m, 2H), 7.50-7.40 (m, 2 H), 7.24 (d, J=8.0 Hz, 1H), 7.29 (d, J=8.0 Hz, 1H), 4.56 (s, 2H), 3.90 (t, J=5.0 Hz, 4 H)), 3.33 (br s, 4H).

Example 3

Synthesis of 4-(6-morpholin-4-ylmethyl-pyridin-3-yl)-naphthalen-1-ylamine hydrochloride via a One-Pot Borylation/Suzuki Coupling of 4-(5-bromo-pyridin-2-yhnethyt)-morpholine

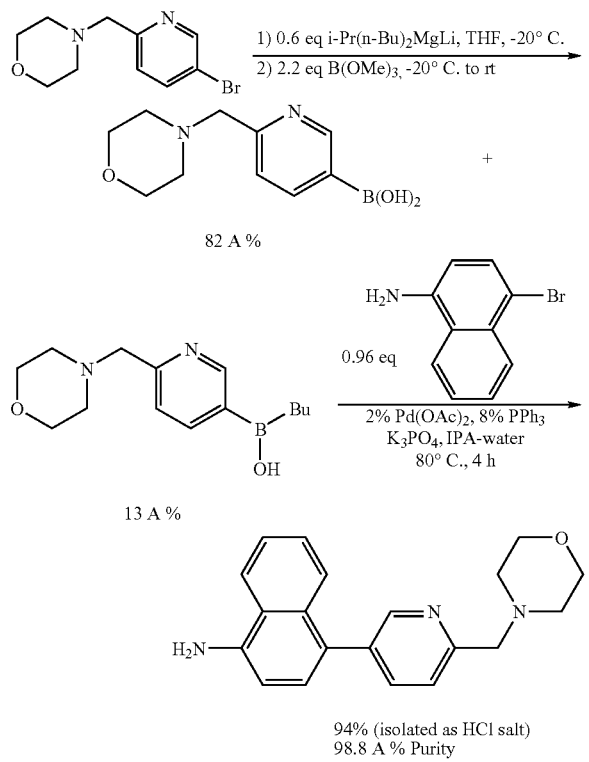

To a solution of 4-(5-bromo-pyridin-2-ylmethyl)-morpholine (16.3 g, 63.4 mmol, 1.0 eq) in anhydrous THF (32 mL) at −20° C. was added a solution of i-Pr(Bu)$_2$MgLi (prepared by adding 2.5 M n-BuLi in hexanes (30 mL, 76.0 mmol, 1.2 eq) to a solution of 2 M i-PrMgCl (19 mL THF solution, 38.0 mmol, 0.6 eq) in THF (30 mL) at 0° C.) dropwise keeping the temperature at −20±2° C. The reaction mixture was stirred at −20±2° C. for 1 h. A solution of B(OMe)$_3$ (16 mL, 139.5 mmol, 2.2 eq) in THF (16 mL) was added at −18±3° C. After stirring at −18±3° C. for 1h, the reaction mixture was allowed to warm to room temperature A mixture of 4-bromonaphthyl-1-amine (12.7 g, 57.1 mmol, 0.9 eq), Pd(OAc)$_2$ (0.28 g, 1.3 mmol, 0.02 eq), and PPh$_3$ (1.33 g, 5.1 mmol, 0.08 eq) was added, followed by isopropanol (65 mL), and a solution of K$_3$PO$_4$ (54 g, 253.6 mmol, 4.0 eq) in H$_{20}$ (65 mL). The mixture was heated to 80±5° C. while distilling the lower boiling point solvents. After stirring for 3 h, the isopropanol was distilled heating up to 92±2° C. The reaction mixture was allowed to cool to 30±2° C before adding isopropyl acetate (130 mL) and 1-methylimidazole (5.1 mL, 64.3 mmol, 1.0 eq). After 30 mm, H$_2$O (40 mL) was added. The organic layer was washed with H$_2$O (80 mL) twice, and filtered through a 0.2 μm nylon filter MeOH (25 mL) was added to the organic solution followed by 37% HCl (5.7 mL, 69.7 mmol, 1.1 eq). After stirring at room temperature for a couple of hours, the precipitated product was collected by filtration, rinsed with 5% MeGH in isopropyl acetate. After drying under vacuum, the HCL salt of the title compound was obtained as a yellow solid (19.0 g, 94% yield, 98.9 A % purity).

Example 4

Synthesis of 4-(6-morpholin-4-ylmethyl-pyridin-3-yl)-naphthalen-1-ylamine hydrochloride salt via Vinamidinium Route

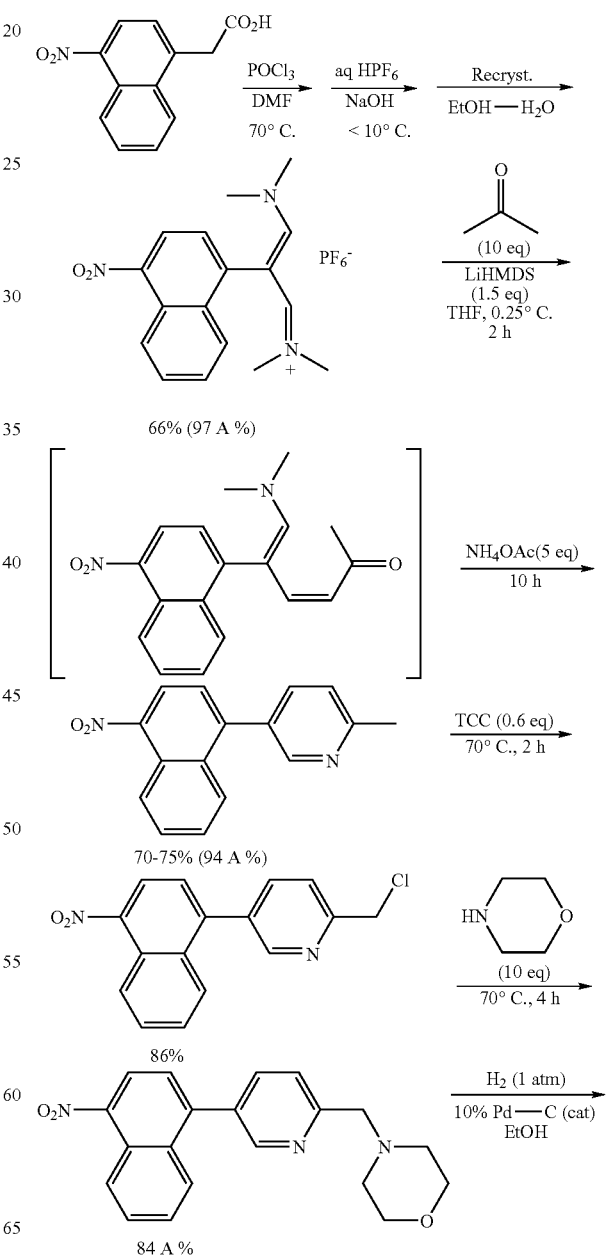

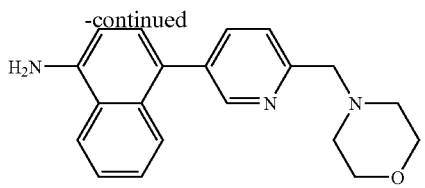

A 100 mL dry flask was flushed with argon. The flask was charged with (4-nitro-naphthalen-1-yl)-acetic acid (13.87 g, 60 mmol) and DMF (30 mL) and then heated to 70° C. POCl$_3$ (11.19 mL, 120 mmol) was added slowly during 2 h to maintain the temperature at 70° C. After 18 h at 70° C., HPLC showed the starting material was consumed. The reaction mixture was cooled to room temperature. The reaction mixture and 5N NaOH (33.6 mL) were added concurrently over 1 h to a mixture of 60% hexafluorophosphoric acid (9.73 mL, 66 mmol) and 5 N NaOH (18 mL) in water (72 mL), maintaining the temperature below 10° C. The reaction flask was rinsed with DMF and added to the mixture. The yellow suspension was stirred for 2 h. The solid product was separated by filtration and washed with water. The yellow product was dried in vacuo at room temperature to give 26 g of crude product as a yellow solid (98%).

A 500 mL flask was charged with the crude material from above (26 g), EtOH (325 mL) and water (32.5 mL). The suspension became homogeneous when it was heated to 70° C. and held for 30 min. The solution was cooled to 0° C. and product was precipitated out. The product was separated by filtration and washed with cool EtOH. The product was dried in vacuo at room temperature to obtain 17.77 g of 2-(4-nitronaphthalen-1-yl)-1,3-bis(dimethylamino)trimethinium hexafluorophosphate as a yellow solid. The yield was 66% with 97 A % purity. $^1$H NMR (400 MHz, DMSO): δ=8.44 (d, 1H, J=8.0 Hz), 8.35 (d, 1 H, J=8.0 Hz), 8.03-8.00 (m, 3 H), 7.91-7.86 (m, 2 H), 7.69 (d, 1 H, J=8.0 Hz), 3.26 (s, 6 H), 2.16 (s, 6 H).

A 250 mL dry flask was flushed with argon. The flask was charged with 2-(4-nitronaphthalen-1-yl)-1,3-bis(dimethylamino)trimethinium hexafluorophosphate (95 w %, 7.24 g, 15.529 mmol), acetone (4.50 g, 77.645 mmol), THF (60 mL) and cooled down to 0° C. LiHMDS (23.3 mL, 23.3 mmol) was added slowly during 1 h. The mixture was then stirred for 30 min at 0° C. and then warmed to room temperature. After stirring for 2 h at room temperature, HPLC showed about 73 A % intermediate was generated. NH$_4$OAc (5.98 g, 77.645 mmol) dissolved in water (15 mL) was added and the reaction mixture was heated to reflux. After reflux for 18 h, product was formed in 80.7 A %. The reaction mixture was cooled to room temperature and the organic phase was separated. The organic solution was diluted with EtOAc (50 mL) and washed with water (2×30 mL). The organic phase was concentrated to give a brown solid. The product was purified by column chromatography to afford 2.57 g of 2-methyl-5-(4-nitro-naphthalen-1-yl)-pyridine as a yellow solid (63.4%). $^1$H NMR (400 MHz, CDCl$_3$): δ=8.62-8.61 (m, 2 H), 8.26 (d, 1 H, J=8.0 Hz), 7.91 (d, 1 H, J=8.8 Hz), 7.78-7.69 (m, 2 H), 7.60 (m, 1 H), 7.48 (d, 1 H, J=7.6 Hz), 7.36 (d, 1 H, J=7.6), 2.70 (s, 3 H).

A 100 mL flask was charged with 2-methyl-5-(4-nitro-naphthalen-1yl)-pyridine (1.848 mg, 7 mmol) and trichloroisocyanuric acid (TCC) (976 mg, 4.2 mmol). Chlorobenzene (22 mL) was added and the mixture was heated to 70° C. After 40 min, 84.5 A % 2-chloromethyl-5-(4-nitro-naphthalen-1yl)-pyridine and 7.6 A % 2-dichloromethyl-5-(4-nitro-naphthalen-1yl)-pyridine were obtained with 7.2 A % 2-methyl-5-(4-nitro-naphthalen-1yl)-pyridine remaining. The suspension was separated by filtration and washed with hot chlorobenzene. To the filtrate, morpholine (6.098 g, 70 mmol) was added and the mixture was heated to 70° C. After 4.5 h, the desired product was formed in 82.4 A %. The reaction mixture was cooled to room temperature. The solid was removed by filtration and was washed with chlorobenzene. Most of the morpholine and solvent were removed on a rotary evaporator. Chlorobenzene (20 mL) was added and evaporated on the rotary evaporator. Isopropyl acetate (IPAc,25 mL) was added to the residue and extracted with water (2×15 mL). To the organic phase, 1 mL MeOH was added, followed by slow addition of 0.5 mL of HCl (37 w %) at room temperature. A yellow solid product was precipitated out. The solid was separated by filtration and washed with i-PrOAc/MeOH (20/1, 15 mL). After drying, 1.943 g of 4-[5-(4-nitro-naphthalen-1-yl)-pyridin-2-ylmethyl]-morpholine HCl salt was obtained as a yellow solid in 73.6% and 97.7A % purity. $^1$H NMR (400 MHz, DMSO): δ=8.83 (s, 1H), 8.45-8.40 (m, 2 H), 8.16 (m, 1 H), 8.00-7.88 (m, 3 H), 7.82-7.71 (m, 2 H), 4.65 (s, 2H), 3.95 (s, 4H), 3.42 (s, 4 H).

A 100 mL flask was charged with 4-[5-(4-nitro-naphthalen-1-yl)-pyridin-2-ylmethyl]-morpholine HCl salt (1.5 g, 3.888 mmol), 10 w % palladium on active carbon (803 mg, 0.3888 mmol) and 60 mL EtOH were added. The flask was degassed and filled with H$_2$ three times. After stirring overnight at room temperature, the carbon was removed by filtration. The filtrate was concentrated. To the residue, EtOAc/MeOH (10/1, 20 mL) was added and the mixture was stirred at room temperature. A yellow solid was precipitated out. The product was separated by filtration. The cake was washed with EtOAc (10 mL). After drying, 1.187 g of the title compound was obtained. The yield was 85.7% with 95 A % purity.

The invention claimed is:

1. A process of making a compound of the formula (I):

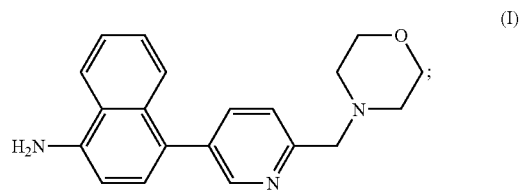

said process comprising:
in one pot reacting 5-bromo-2-[(4-morpholino)methyl]pyridine compound (e) with i-Pr(n-Bu)$_2$MgLi under suitable temperature and solvent conditions, subsequently adding B(OMe)$_3$, then adding Pd(OAc)$_2$, PPh$_3$, K$_3$PO$_4$, IPA, and 1-amino-4-bromonaphthalene (a) and subsequently adding HCl, IPAc and MeOH at ambient temperature to provide compound (I) as an HCl salt, and converting the HCl salt of compound (I) to the free base of compound (I) by treatment with a base where prior to the addition of HCl, IPAc and MeOH, the reaction is conducted in one pot and no intermediates are isolated:

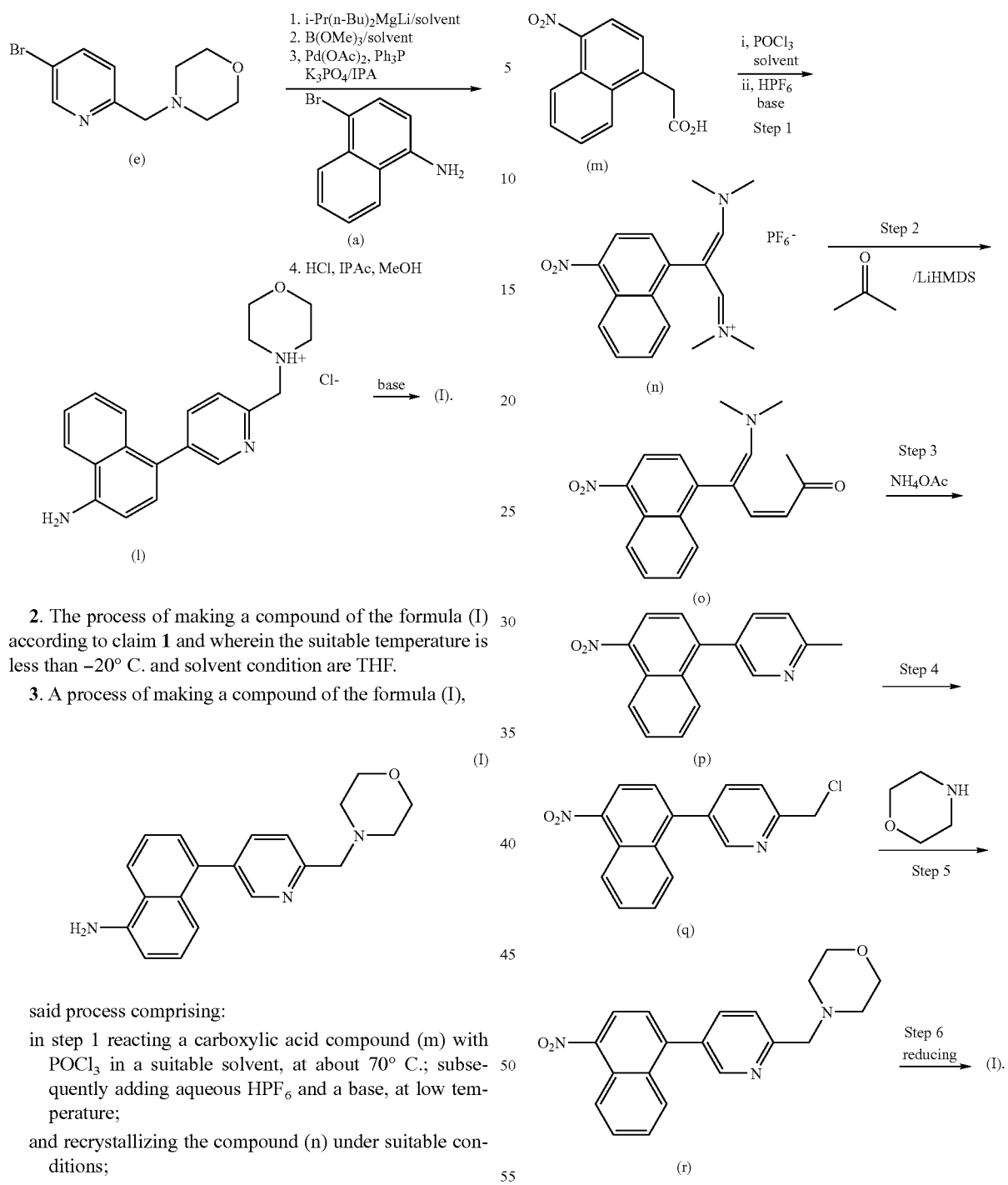

2. The process of making a compound of the formula (I) according to claim 1 and wherein the suitable temperature is less than −20° C. and solvent condition are THF.

3. A process of making a compound of the formula (I), (I)

said process comprising:
- in step 1 reacting a carboxylic acid compound (m) with POCl₃ in a suitable solvent, at about 70° C.; subsequently adding aqueous HPF₆ and a base, at low temperature; and recrystallizing the compound (n) under suitable conditions;
- in step 2 reacting the compound (n) obtained from step 1 with acetone and LiHMDS in a suitable solvent at about 0-25° C. to produce intermediate (o);
- in step 3 adding ammonium acetate to (o) to produce compound (p), subsequently in step 4 chlorinating (p) with a suitable agent under suitable conditions, to produce compound (q);
- adding morpholine in step 5 under suitable conditions, to produce nitro compound (r) wherein steps (3)-(5) are conducted in a single pot, and subsequently reducing (r) in step 6 under suitable conditions to produce (I):

4. The process of making a compound of the formula (I) according to claim 3 wherein:
- in step 1, the solvent is DMF, the base is NaOH, the low temperature is about <10° C. and the recrystallizing conditions are EtOH/H₂O;
- in step 2 the solvent is THF;
- in step 4 the suitable agent is TCC, the suitable conditions are about 7020 C.;
- in step 5 the suitable conditions are about 70° C.; and in step 6 under suitable conditions are H₂ (1 atm) and a catalyst, Pd on carbon.

5. A process of preparing a compound of formula (I) according to a reaction scheme set forth below,

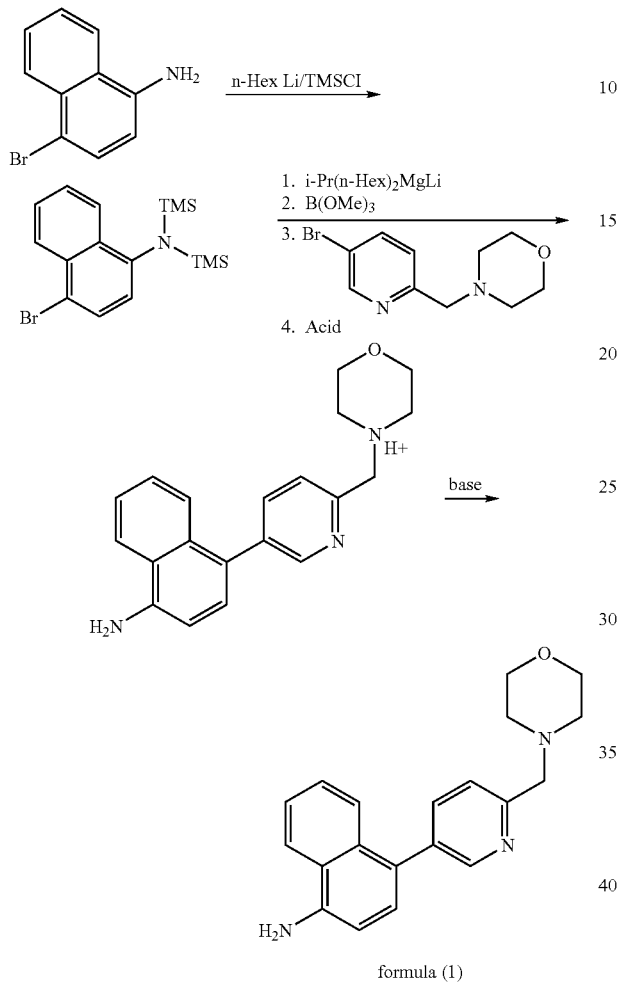

formula (1)

comprising:

step a: 1-amino-4-bromonaphthalene is reacted with n-hexyllithium (n-HexLi) and chlorotrimethylsilane (TMSCl) in a suitable solvent and under a temperature between 0° and 20° to provide 1-N,N-bis(trimethylsilyl)-amino-4-bromonaphthalene;

step b: in one pot, 1-N,N-bis(trimethylsilyl)-amino-4-bromonaphthalene is reacted with a mixture of i-PrMgCl and n-hexyllithium under a suitable temperature to form a 1-N,N-bis(trimethylsilyl)-amino-4-naphthyl anion; the resulting 1-N,N-bis(trimethylsilyl)-amino-4-naphthyl anion is reacted with trimethylborate to provide an intermediate compound of 1-N,N-bis(trimethylsilyl)-amino-4-naphthyl boronic acid; the resulting 1-N,N-bis(trimethylsilyl)-amino-4-naphthyl boronic acid is reacted with 4-((5-bromopyridin-2-yl)methyl)morpholine under suitable conditions to form 4-(6-(morpholinomethyl)pyridin-3-yl)naphthalen-1-amine, and subsequently in a different pot, the resulting 4-(6-(morpholinomethyl)pyridin-3-yl)naphthalen-1-amine is treated with a suitable acid to provide a salt of 4-(6-(morpholinomethyl)pyridin-3-yl)naphthalen-1-amine; and step c: the resulting salt of 4-(6-(morpholinomethyl)pyridin-3-yl)naphthalen-1-amine is treated with a suitable base to provide a compound of formula (I).

6. The process of preparing a compound of formula (I) according to claim 5, wherein the suitable solvent of step a is methyl tert-butyl ether (MTBE), the suitable temperature of step b is about −20°, the suitable conditions of step b are Pd(OAc)₂, PPh₃, K₂CO₃, and isopropyl (IPA), the suitable acid of step b is hydrochloric acid, and the suitable base of step c is sodium hydroxide.

7. A process of preparing a compound of formula (I) according to a reaction scheme set forth below,

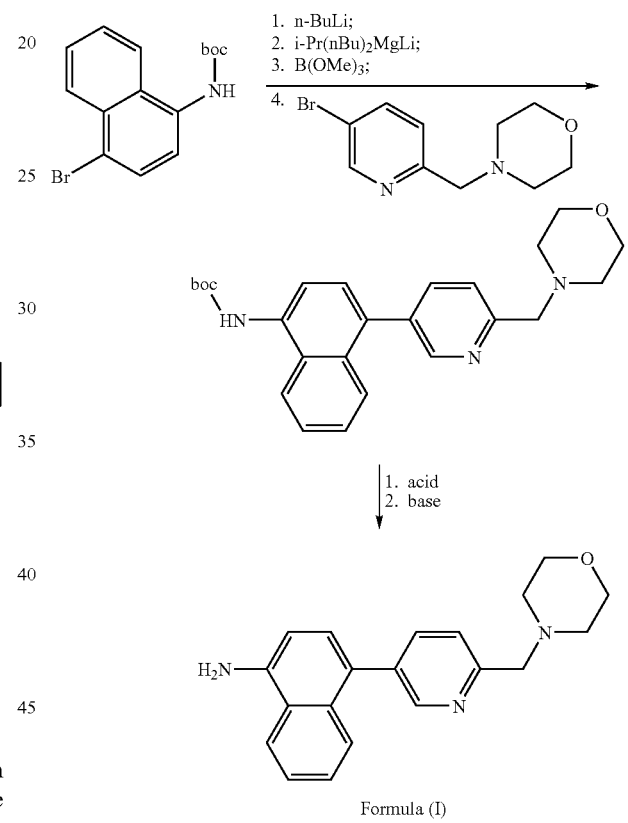

Formula (I)

comprising:

step a: in one pot, N-Boc-4-bromonaphthyl-1-amine is reacted with n-BuLi in a first suitable solvent to provide a deprotonated intermediate; the resulting deprotonated intermediate is then reacted with i-Pr(nBu)₂MgLi in a second suitable solvent to provide a corresponding anion via bromo-magnesium exchange; the resulting anion is then reacted with trimethylborate to provide an intermediate of corresponding boronic acid; and the resulting boronic acid is reacted with 4-((5-bromopyridin-2-yl)methyl)morpholine to provide tert-butyl 4-(6-(morpholinomethyl)pyridin-3-yl)naphthalen-1-ylcarbamate; and step b: subsequently in a different pot, the resulting tert-butyl 4-(6-(morpholinomethyl)pyridin-3-yl)naphthalen-1-ylcarbamate is reacted with a suitable acid to remove the Boc protection group and subsequently basified with a suitable base to provide the compound of formula (I).

8. The process of preparing a compound of formula (I) according to claim 7 wherein the first suitable solvent of step a is methyl tert-butyl ether (MTBE), and the second suitable solvent of step a is tetrahydrofuran (THF).

* * * * *

UNITED STATES PATENT AND TRADEMARK OFFICE
CERTIFICATE OF CORRECTION

PATENT NO. : 7,714,127 B2  Page 1 of 1
APPLICATION NO. : 11/538465
DATED : May 11, 2010
INVENTOR(S) : Guisheng Li et al.

It is certified that error appears in the above-identified patent and that said Letters Patent is hereby corrected as shown below:

In Column 20, in line sixty six of Claim 4, change "7020" to --70°--.

Signed and Sealed this

Thirty-first Day of August, 2010

David J. Kappos
*Director of the United States Patent and Trademark Office*